(12) United States Patent
Zhang et al.

(10) Patent No.: US 11,260,068 B2
(45) Date of Patent: Mar. 1, 2022

(54) LONG-CIRCULATING LIPOSOME MODIFIED WITH C(RGD-ACP-K)

(71) Applicant: BEIJING GREATSUN BIO-PHARM. TECH. CO., LTD, Beijing (CN)

(72) Inventors: Qiang Zhang, Beijing (CN); Cuishuan Wu, Beijing (CN); Yue Su, Beijing (CN); Changjin Lee, Gangwon-Do (KR); Guanghua Cui, Beijing (CN)

(73) Assignee: BEIJING GREATSUN BTO-PHARM. TECH. CO., LTD, Beijing (CN)

( * ) Notice: Subject to any disclaimer, the term of this patent is extended or adjusted under 35 U.S.C. 154(b) by 0 days.

(21) Appl. No.: 16/616,651

(22) PCT Filed: May 24, 2018

(86) PCT No.: PCT/CN2018/088251
§ 371 (c)(1),
(2) Date: Nov. 25, 2019

(87) PCT Pub. No.: WO2018/214944
PCT Pub. Date: Nov. 29, 2018

(65) Prior Publication Data
US 2020/0197424 A1    Jun. 25, 2020

(30) Foreign Application Priority Data

May 25, 2017    (CN) .......................... 201710379667.0

(51) Int. Cl.
*A61K 31/704*    (2006.01)
*A61K 47/64*    (2017.01)
*A61K 9/127*    (2006.01)

(52) U.S. Cl.
CPC .......... *A61K 31/704* (2013.01); *A61K 9/1271* (2013.01); *A61K 47/64* (2017.08)

(58) Field of Classification Search
CPC .... A61K 31/704; A61K 47/64; A61K 9/1271; A61K 9/127; A61K 47/6911;
(Continued)

(56) References Cited

U.S. PATENT DOCUMENTS

| 2012/0141380 A1 | 6/2012 | Margel et al. |
| 2014/0154298 A1* | 6/2014 | Hong .................... A61K 47/28 424/417 |

(Continued)

FOREIGN PATENT DOCUMENTS

| CN | 1846691 A | 10/2006 |
| CN | 10132790 | * 7/2008 |

(Continued)

OTHER PUBLICATIONS

Allen, T. M., et al. in BBA, 1237, pp. 99-108, 1995.*

(Continued)

*Primary Examiner* — Gollamudi S Kishore
(74) *Attorney, Agent, or Firm* — Hoxie & Associates LLC (57) ABSTRACT

The present invention relates to a long-circulating liposome modified with c(RGD-ACP-K). The present invention pertains to the field of pharmaceutical preparations, in particular to the field of targeted pharmaceutical preparations. More specifically, the present invention relates to a long-circulating liposome, the surface of the liposome being modified with c(RGD-ACP-K), and the liposome comprising doxorubicin or a pharmaceutically acceptable salt thereof such as doxorubicin hydrochloride as an anti-cancer active agent. The long-circulating liposome can targetedly deliver the anti-cancer active agent into tumor neovascular endothelial cells and tumor cells and can prolong the circulation time of the liposome in vivo, thereby enhancing the therapeutic effect of anti-tumor medicaments.

19 Claims, 4 Drawing Sheets

(58) Field of Classification Search
CPC ........ A61K 47/62; A61K 47/42; A61K 45/06; A61P 35/00; A61P 35/02
See application file for complete search history.

(56) References Cited

U.S. PATENT DOCUMENTS

2016/0279252 A1* 9/2016 Aswad ................... A61K 47/60
2016/0317670 A1 11/2016 Broome et al.

FOREIGN PATENT DOCUMENTS

| CN | 101327190 A | 12/2008 |
| CN | 102114000 A | 7/2011 |
| CN | 103371975 A | 10/2013 |
| CN | 105663043 A | 6/2016 |
| CN | 106699845 A | 5/2017 |
| EP | 1 002 543 A1 | 5/2000 |
| KR | 20130128284 A | 11/2013 |

OTHER PUBLICATIONS

Galior, et al., "Titin-Based Nanoparticle Tension Sensors Map High-Magnitude Integrin Forces within Focal Adhesions," Supporting Information, *Department of Chemistry & Department of Physics, Emory University*, 12 pages; *Nano Lett.*, vol. 16, No. 1, 15 pages, (2016), obtained from https://www.ncbi.nlm.nih.gov/pmc/articles/PMC5592801/ on Apr. 9, 2020.

Kibria, et al., "Dual-ligand Modification of PEGylated Liposomes Shows Better Cell Selectivity and Efficient Gene Delivery," *Journal of Controlled Release*, 32 pages, (2011); DOI: 10.1016/j.jconrel.2011.03.012.

Li, et al., "Efficient Delivery of Docetaxel for the Treatment of Brain Tumors by Cyclic RGD-tagged Polymeric Micelles," *Molecular Medicine Reports*, vol. 11, pp. 3078-3086, (2015); DOI: 10.3892/mmr.2014.3017.

Park, et al., "Cyclic RGD Peptides Incorporating Cycloalkanes: Synthesis and Evaluation as PET Radiotracers for Tumor Imaging," *ACS Medicinal Chemistry Letters*, vol. 5, No. 9, pp. 979-982, (2014).

Park, et al., "Improved Tumor-targeting MRI Contrast Agents: Gd(DOTA) Conjugates of a Cycloalkane-based RGD Peptide," *Biochemical and Biophysical Research Communications*, vol. 455, pp. 246-250, (2014).

Written Opinion of the International Searching Authority for International Application No. PCT/CN2018/088251, English Translation, dated Aug. 7, 2018, 7 pages.

Xu, et al., "Development of Targeted Therapies in Treatment of Glioblastoma," *Cancer Biol. Med.*, vol. 12, pp. 223-237, (2015); DOI: 10.7497/j.issn.2095-3941.2015.0020.

Bardania et al., "Encapsulation of eptifibatide in RGD-modified nanoliposomes improves platelet aggregation inhibitory activity," Journal of Thrombosis and Thrombolysis, vol. 43, No. 2, pp. 184-193, (2017); DOI: 10.1007/s11239-016-1440-6.

Chen et al., "Peptide-22 and Cyclic RGD Functionalized Liposomes for Glioma Targeting Drug Delivery Overcoming BBB and BBTB," ACS Applied Materials & Interfaces, vol. 9, No. 7, pp. 5864-5873, (2017).

Janssen et al., "Peptide-targeted PEG-liposomes in anti-angiogenic therapy," International Journal of Pharmaceutics, vol. 254, pp. 55-58, (2003).

Park et al., "Synthesis and evaluation of new c(RGD) peptides for tumor-targeting PET imaging probe," Journal of Labelled Compounds and Radiopharmaceuticals, vol. 56, No. Suppl. 1, pp. S206, (2013), 3 pages. Abstract only.

Schiffelers et al., "Anti-tumor efficacy of tumor vasculature-targeted liposomal doxorubicin," Journal of Controlled Release, vol. 91, No. 1-2, pp. 115-122, (2003).

* cited by examiner

LONG-CIRCULATING LIPOSOME MODIFIED WITH C(RGD-ACP-K)

CROSS-REFERENCE TO RELATED APPLICATIONS

This application is a National Stage Entry under 35 U.S.C. § 371 of International Application No. PCT/CN2018/088251, filed May 24, 2018, which claims the benefit of priority from Chinese patent application No. 201710379667.0, filed on May 25, 2017, the contents of each of which are incorporated herein by reference in their entireties.

TECHNICAL FIELD

The invention belongs to the field of pharmaceutical preparation, in particular to the field of targeted pharmaceutical preparation. More specifically, the invention relates to a long-circulating liposome, which is modified on its surface with cyclic [RGD-(1S,3R)-3-aminocyclopentanecarboxylic acid] (abbreviated to c(RGD-ACP-K)). The liposome is useful as a targeted delivery carrier of an anti-cancer agent. For example, the liposome may comprise doxorubicin or a pharmaceutically acceptable salt thereof, such as doxorubicin hydrochloride, as an anti-cancer agent. The long-circulating liposome is capable of targetedly delivering an anti-cancer agent into tumor neovascular endothelial cells and tumor cells, and can prolong the circulation time of the liposome in vivo, thereby enhancing the therapeutic effect of the anti-cancer agent.

BACKGROUND OF THE INVENTION

Doxorubicin, also known as adriamycin, is an anthracycline antibiotic extracted from *Streptomyces peucetius* var. *caesius* in 1969, and has strong anti-cancer activity. Doxorubicin can be clinically used alone or in combination with other anti-cancer agents to effectively treat various malignant tumors. It is usually used in the form of doxorubicin hydrochloride, which has the chemical structure below:

Doxorubicin or a pharmaceutically acceptable salt thereof (e.g., doxorubicin hydrochloride) is a cell cycle phase nonspecific drug, and prevents DNA replication, inhibits the action of DNA-dependent polymerase, and interfers with RNA transcription process mainly by intercalating between DNA base pairs and tightly binding to DNA. Its effect of preventing cell division is not selective for tumor cells relative to normal cells. Thus, like most chemotherapeutic agents, doxorubicin hydrochloride has many adverse effects. Besides the common adverse effects such as emesis, nausea and hair loss, it causes severe dose-dependent cardiotoxicity due to the fact that this compound has a significantly higher affinity with the myocardium than other tissues, and can damage the cardiomyocytes through the semiquinone metabolite. This explains why its clinical applications are largely limited. Although the cardiotoxicity of doxorubicin anti-tumor agents can be alleviated to some extent by reducing the cumulative dosage, the suppressive effect on tumors would be correspondingly reduced.

In order to alleviate the cardiotoxicity of doxorubicin hydrochloride and reduce its adverse effects, Elan developed doxorubicin hydrochloride liposome injection Myocet (also known as Evacet), which is mainly used for treating metastatic breast cancer, has the specification of 20 mg/10 mL or 50 mg/20 mL per bottle and is also administered by intravenous infusion generally in a period of one hour. The administration is carried out at a dosage of 20-50 mg·m$^{-2}$ with an interval of three weeks for 3 to 6 months. It's common adverse effects inlcude erythrocytopenia, thrombocytopenia, gingival hemorrhage, epistaxis, emesis, nausea, diarrhea, or the like. Myocet has less risk of developing cardiotoxicity than conventional doxorubicin hydrochloride injections, but is easily uptaken by macrophages in liver and spleen and thus is rapidly eliminated, resulting in a short retention time in the body and a low therapeutic effect.

Long-circulating liposomes are prepared by additionally modifying the surface of the conventional delivery system with hydrophilic polyethylene glycol (PEG). The long-circulating delivery system is capable of evading the action of opsonins in plasma so as to avoid uptake by macrophages (for this reason, a long-circulating delivery system modified with polyethylene glycol is also known as a stealth delivery system), thereby significantly increasing its retention time in the circulatory system and the blood concentration. Long-circulating delivery systems can increase the accumulation of loaded drugs into tumor tissue via the EPR effect (i.e., the enhanced permeability and retention effect of solid tumors), thereby increasing the targeted delivery of an anti-cancer agent. The microvascular endothelium in normal tissues is dense and structurally intact, so it is uneasy for macromolecules and lipid particles to penetrate the vessel wall. However, solid tumor tissue is rich in blood vessels, has wide blood vessel wall gap and poor structural integrity, and lacks lymphatic reflux, resulting in selective high permeability and retention for macromolecules and lipid particles. This phenomenon is known as the high permeability and retention effect of solid tumors, and is also referred to as the EPR effect for short. Based on the aforesaid mechanism, Sequs from USA developed and launched the doxorubicin loaded PEG-modified long-circulating liposome (trade name: Doxil); ALZA and Schering-Plough jointly developed and launched another doxorubicin loaded PEG-modified long-circulating liposome (trade name: Caelyx). The doxorubicin loaded PEG-modified long-circulating liposomes are characterized in that doxorubicin is encapsulated in the stealth liposome delivery system. Since the surface of the long-circulating liposome is covered with a layer of PEG, it is prevented from being recognized and phagocytized by the immune system in the body, so that the drug can be circulated in the body for several days, thereby increasing the anti-tumor action time of doxorubicin.

Long-circulating liposomes can significantly increase the circulation time of a drug in the body. Due to the enhanced EPR effect of tumor tissue for long-circulating liposomes, drug-loaded long-circulating liposomes can passively accumulate in tumor tissue. However, since the target of most anti-cancer agents is within tumor cells, the accumulation of anti-cancer agents in tumor tissue does not mean the increased drug concentration within tumor cells. Thus, the key to improve therapeutic effect is to improve the efficiency of the delivery of an anti-cancer agent into tumor cells.

Chinese Patent No. 200510063388.0 relates to an anti-cancer agent loaded long-circulating liposome for injection, which is modified with both polyethylene glycol (PEG) and linear polypeptide fragment containing the sequence arginine-glycine-aspartate (RGD) or linear RGD analog (an integrin ligand), and said anti-cancer agent may be, for example, adriamycin (i.e., doxorubicin), daunorubicin, paclitaxel, cisplatin, and the like. The patent achieves the targeted delivery of an anti-cancer agent to tumors based on the principle that linear RGD can be recognized by integrin on the surface of tumor cells, thereby mediating adhesion to tumor cells. The patent believes that although both linear and cyclic RGD peptides specifically bind to integrin $\alpha_v\beta_3$, the mechanisms of action of these two peptides are different. The target of cyclic RGD peptides lies in tumor neovascularization rather than tumor cells, and cyclic RGD peptides exert an anti-tumor effect by destroying the tumor neovascularization to cut off the nutrients and oxygen supply to the tumor, while the target of linear RGD peptides is the tumor cells themselves, and the anti-tumor effect thereof is achieved by increasing the uptake of the anti-cancer agent by tumor cells. Therefore, in order to enhance the targeting of anti-cancer agents to tumor cells, the invention protected by the patent is a liposome modified with a linear RGD peptide.

Studies have shown that cyclic RGD peptides have better affinity, receptor selectivity and enzyme stability for integrin $\alpha_v\beta_3$ than linear RGD peptides. At present, the main researches focus on the application of cyclic RGD peptides. In fact, almost all RGD modifications made to tumor diagnostic reagents that have entered clinical research utilize cyclic RGD peptides. Among them, c(RGDfk) is reported more, and is recognized to be a better target molecule. For example, US Patent Application US2012/0141380A1 reported a nanoparticle consisting of a polymer, which was modified with the cyclic RGD peptide c(RGDfk), wherein said polymer was a metal chelating agent coated with a magnetic metal oxide, and at least one active agent was covalently bonded to the polymer.

In addition, Ji-Ae Park et al. (Ji-Ae Park et al., Cyclic RGD Peptides Incorporating Cycloalkanes: Synthesis and Evaluation as PET Radiotracers for Tumor Imaging. *ACS Medicinal Chemistry Letters* 2014, 5, 979-982) reported that cyclic [RGD-(1S,3R)-3-aminocyclopentanecarboxylic acid] (abbreviated to c(RGD-ACP-K)) and cyclic [RGD-(1S,3R)-3-aminocyclohexanecarboxylic acid] (abbreviated to c(RGD-ACH-K)) had high affinity toward U87MG glioblastoma cells expressing integrin $\alpha_v\beta_3$, and that binding of c(RGD-ACP-K) and c(RGD-ACH-K) to integrin $\alpha_v\beta_3$ on the surface of U87MG cells was superior to that of the cyclic peptide c(RGDyK) as a reference, and the binding of c(RGD-ACP-K) was significantly higher than that of c(RGD-ACH-K). However, after c(RGD-ACP-K) and c(RGD-ACH-K) were prepared into the conjugates c(RGD-ACP-K)-DOTA-$^{64}$Cu and c(RGD-ACH-K)-DOTA-$^{64}$Cu, respectively, PET imaging showed that the in vivo targeting of the former was worse than that of the latter, and even worse than that of the reference c(RGDyK)-DOTA-$^{64}$Cu (see FIG. 4 of this document). Thus, the binding affinities of c(RGD-ACP-K) and c(RGD-ACH-K) in vitro are not the same as those in vivo, and there is no correlation between the in vitro profile and the in vivo profile.

Therefore, there is still a need for molecules well targeting to tumor cells and an anti-cancer agent delivery system prepared therefrom that has an improved targeting property and reduced adverse effects.

DESCRIPTION OF THE INVENTION

The inventors studied and compared a variety of linear and cyclic RGD sequences with the hope to obtain a target molecule that is comparable or superior to c(RGDfk) in terms of targeting property for the preparation of a targeted delivery system of anti-cancer agents. The inventors have surprising found that not all cyclic RGD peptides have significant targeting when they are used to modify liposomes, and the targeting property of many cyclic RGD sequences is not evident, but the long-circulating liposome modified with the specific cyclic RGD peptide, c(RGD-ACP-K), is significantly more targeted to tumor cells than those modified with other linear and cyclic RGD peptides including c(RGDfk). Accordingly, for the first time, the inventors used the cyclic RGD peptide c(RGD-ACP-K), which was only used for diagnostic research before, to modify a liposome. The liposome modified by this cyclic peptide had excellent targeting property. Although the liposome did not remarkably improve the delivery of cisplatin, it has excellent improvement on the delivery of the anti-cancer agent doxorubicin hydrochloride.

Furthermore, the inventors have surprisingly found that, differently from the reports in the prior art, the long-circulating liposome modified with c(RGD-ACP-K) targets not only tumor neovascularization, but also tumor cells themselves, and allows targeted delivery of an anti-cancer agent into the interior of tumor cells, resulting in unexpectedly better delivery efficiency and therapeutic effect. Even more surprisingly, said liposome also has the following advantages:

1) c(RGD-ACP-K) is significantly better in terms of in vitro targeting property to tumors than c(RGDfk), which is currently known as one of the best targeting RGD peptides. The long-circulating liposome modified with c(RGD-ACP-K) has better in vitro targeting property to tumors than the long-circulating liposome modified with c(RGDfk), and the in vivo anti-cancer effect of the long-circulating liposome modified with c(RGD-ACP-K) is significantly superior to that of the long-circulating liposome modified with c(RGDfk). Thus, the in vivo result is consistent with in vitro result, and there is remarkable correlation between them.
2) The long-circulating liposome modified with c(RGD-ACP-K) targets not only tumor cells with high expression of integrin ave, but also tumor cells with low expression of integrin $\alpha_v\beta_3$, which indicates that the targeting property of the long-circulating liposome modified with c(RGD-ACP-K) to tumor cells involves an unknown mechanism other than recognition by integrin $\alpha_v\beta_3$, allowing it to target more types of tumors and be a better drug delivering carrier.
3) The toxicity of the doxorubicin hydrochloride loaded long-circulating liposome modified with c(RGD-ACP-K) on the heart is reduced.
4) The long-circulating liposome modified with c(RGD-ACP-K) has a better delivery effect on doxorubicin hydrochloride than on cisplatin.

Accordingly, the invention provides a long-circulating liposome targeting tumors, which is modified on its surface with c(RGD-ACP-K), wherein said c(RGD-ACP-K) is linked to PEG via a chemical bond, and said PEG is linked to a phospholipid on the surface of the liposome. The liposome can targetedly deliver an anti-cancer agent into the interior of tumor neovascular endothelial cells and tumor cells, and can prolong the circulation time of the drug delivery system in the body, thereby enhancing the anti-tumor effect of the anti-cancer agent.

In one embodiment, the long-circulating liposome described above is provided, wherein said c(RGD-ACP-K) is linked to PEG via a chemical bond, said PEG is linked to a phospholipid on the surface of the liposome, and said phospholipid is selected from those phospholipids contained in the phospholipid-PEG described herein, such as distearoyl phosphatidylcholine (DSPC), phosphatidylethanolamine (PE), distearoyl phosphatidylethanolamine (DSPE), and phosphatidylcholine (PC).

In one embodiment, the long-circulating liposome described above is provided, wherein said c(RGD-ACP-K) is linked to PEG via a chemical bond, and said PEG is linked to DSPE on the surface of the liposome.

In one embodiment, the long-circulating liposome described above is provided, characterized in that the surface of the liposome is modified with c(RGD-ACP-K), wherein said c(RGD-ACP-K) is linked to PEG via a chemical bond, said PEG is linked to a phospholipid on the surface of the liposome, and the liposome comprises an anti-cancer agent.

In a preferred embodiment, the long-circulating liposome described above is provided, characterized in that the surface of the liposome is modified with c(RGD-ACP-K), wherein said c(RGD-ACP-K) is linked to PEG via a chemical bond, said PEG is linked to a phospholipid on the surface of the liposome, and the liposome comprises doxorubicin or a pharmaceutically acceptable salt thereof, such as doxorubicin hydrochloride, as an anti-cancer agent.

Since the long-circulating liposome is modified on its surface with PEG, it can escape from the capture of the reticuloendothelial system in the body so that the circulation time of the long-circulating liposome in the body is prolonged. The target molecule c(RGD-ACP-K) is linked to the terminal of PEG, so that the action of PEG and the recognition of the drug delivery system by a receptor are not affected. Moreover, the target molecule c(RGD-ACP-K) is not easy to break upon the formation of the covalent bond.

As used herein, the terms "polyethylene glycol" and "PEG" are interchangeable. The polyethylene glycol has a molecular weight from 200 to 50000, preferably from 1000 to 5000. Examples of polyethylene glycol used in the invention include PEG 1000, PEG 1100, PEG 1200, PEG 1300, PEG 1400, PEG 1450, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750 or PEG 5000.

The phospholipid used to prepare the long-circulating liposome in accordance with the invention is any types of phospholipids known in the art that can be used to prepare a liposome. For example, the phospholipid used to prepare the long-circulating liposome in accordance with the invention may be selected from the group consisting of soybean lecithin, hydrogenated soybean lecithin, dilauroyl lecithin, dimyristoyl lecithin, dipalmitoyl lecithin, distearoyl lecithin, 1-myristoyl-2-palmitoyl lecithin, 1-palmitoyl-2-myristoyl lecithin, 1-palmitoyl-2-stearoyl lecithin, 1-stearoyl-2-palmitoyl lecithin, yolk lecithin, dioleoyl lecithin, dilauroyl phosphatidylglycerol, dipalmitoyl phosphatidic acid, dimyristoyl phosphatidylethanolamine, dipalmitoyl phosphatidylethanolamine, dimyristoyl phosphatidyl serine, dipalmitoyl phosphatidyl di-serine, dipalmitoyl phosphatidylcholine, brain phosphatidyl serine, brain sphingomyelin, dipalmitoyl sphingomyelin, distearoyl sphingomyelin, distearoyl phosphatidylethanolamine (DSPE), or any combination thereof.

As used herein, the terms "phospholipid-polyethylene glycol complex" and "phospholipid-PEG" are interchangeable, and refer to reactive esterified polyethylene glycols, for example, distearoyl phosphatidylcholine-polyethylene glycol (PEG-DSPC), phosphatidylethanolamine-polyethylene glycol (PEG-PE), distearoyl phosphatidylethanolamine-polyethylene glycol (PEG-DSPE), phosphatidylcholine-polyethylene glycol (PEG-PC). The phospholipid-polyethylene glycol complexe can be prepared by a known method in the art, or is commercially available.

As used herein, the term "liposome" refers to a lipid bilayer vesicle prepared from phospholipid and cholesterol as major materials. Methods and materials for preparing liposomes are known in the art. For example, methods for preparing liposomes include passive drug loading methods and active drug loading methods (e.g., See: Preparation methods and research progress of liposomes. 2012 Conference of Professional Committee of Chinese Medicine Preparation of World Federation of Chinese Medicine Societies, and Chinese Medicine Preparation Branch of China Association of Chinese Medicine as well as "Jiangzhong Cup" Chinese Medicine Preparation Innovation and Development Forum). The passive drug loading methods include thin film dispersion, ultrasonic dispersion, film extrusion, injection, freeze-drying, melting, reverse-phase evaporation, surfactant solubilization, re-emulsion, freezing-thawing, microfluidization, centrifugation, spray drying methods and the like. The active drug loading methods include pH gradient method, ammonium sulfate gradient method, calcium acetate gradient method, sodium sulfate gradient method and the like. The active drug loading methods are preferred, and sodium sulfate gradient method is more preferred in the invention.

As used herein, the terms "long-circulating liposome" and "stealth liposome" are interchangeable, and refer to a liposome modified with PEG, which can escape the capture by reticuloendothelial system in the body due to the modification on its surface with PEG, thereby increasing its circulation time in the body.

The chemical name of cholesterol described herein is (3β)-cholest-5-en-3-ol, which is one of the important components in biomembranes. It is a neutral lipid and an amphiphilic molecule, but has greater lipophilicity relative to hydrophilicity. Cholesterol is used to stabilize the phospholipid bilayer membrane of liposomes. The chemical structure of cholesterol is as follows:

Cholesterol is known in the art and is commercially available, for example, from Pharmacia Biotech Inc., USA.

The ratio of phospholipid to cholesterol comprised in the liposome of the invention is 1-1000:1, preferably 1-800:1, 1-500:1, 1-200:1, 1-100:1 or 1-10:1 by weight, more preferably 1-100:1 by weight, most preferably 1-10:1 by weight.

The liposome of the invention may be dispersed in an injectable vehicle for intravenous administration. The injectable vehicle is, for example, 0.9% sodium chloride injection, 5% glucose injection, PBS buffer pH=7.4.

The c(RADfk) described herein has the chemical name of cyclo(Arg-Ala-Asp-d-Phe-Lys), and the chemical structure of c(RADfk) is known in the art and is commercially available, for example, from Qiangyao Biotechnology, Shanghai.

The c(RGDfk) described herein has the chemical name of cyclo(Arg-Gly-Asp-d-Phe-Lys), and the chemical structure of c(RGDfk) is known in the art and is commercially available, for example, from Qiangyao Biotechnology, Shanghai.

The ABHT described herein has the chemical name of C6-4-(3-aminopropoxy)benzoyl-β-HomoTyr[N-(3-propyl)-4-methoxypyridin-2-amine], and the chemical structure of

ABHT is known in the art and is commercially available, for example, from Hangzhou Chinese Peptide.

The c(RGD-AAB-K) described herein has the chemical name of cyclo[RGD-2-((2R,5S)-5-(aminomethyl)-4-(4-(aminomethyl)benzyl)-3,6-dioxopiperazin-2-yl)acetic acid], and the chemical structure of c(RGD-AAB-K) is known in the art and is commercially available, for example, from Hangzhou Chinese Peptide.

The c(RGD-ACP-K) described herein has the chemical name of cyclo[RGD-(1S,3R)-3-aminocyclopentane-1-carboxylic acid], and the chemical structure of c(RGD-ACP-K) is known in the art and is commercially available, for example, from Hangzhou Chinese Peptide.

As used herein, the term "pharmaceutically acceptable" means that which is useful in the preparation of a medicament, which is usually safe, non-toxic, and neither biologically nor otherwise undesirable, and includes that which is acceptable for veterinary and human pharmaceutical use. As used herein, the term "pharmaceutically acceptable salt" means a pharmaceutically acceptable salt that retains the desired pharmacological activity of doxorubicin.

In another aspect, the invention provides a method for preparing the long-circulating liposome in accordance with the invention, comprising the steps of:

(1) Reacting excessive phospholipid-PEG-$R^1$ with c(RGD-ACP-K), terminating the reaction with glycine after c(RGD-ACP-K) is depleted, dialyzing the reaction, and then freeze-drying the reaction to give a lyophilizate, which is a mixture of phospholipid-PEG-c(RGD-ACP-K) and phospholipid-PEG-$R^1$, wherein $R^1$ is succinimidyl ester (-NHS) or benzotriazolyl (-BTC);

(2) Preparing a blank long-circulating liposome from phospholipid, cholesterol, phospholipid-PEG, and the lyophilizate obtained in step (1), wherein the moles of phospholipid-PEG-c(RGD-ACP-K) added account for 4-16% (for example, 4%, 8%, 12% or 16%) of the moles of phospholipid-PEG added;

(3) Incubating the blank long-circulating liposome obtained in step (2) with an anti-cancer agent solution, then passing the reaction through a dextran gel column, eluting and collecting the red liposome portion, and repeatedly extruding it through a 0.22 μm filter membrane, to give the long-circulating liposome modified with c(RGD-ACP-K) in accordance with the invention, wherein said anti-cancer agent is doxorubicin or a pharmaceutically acceptable salt thereof, such as doxorubicin hydrochloride.

In one embodiment, the method described above is provided, wherein the PEG has the molecular weight from 200 to 50000, preferably from 1000 and 5000, more preferably wherein the PEG is PEG 1000, PEG 1100, PEG 1200, PEG 1300, PEG 1400, PEG 1450, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750 or PEG 5000, most preferably wherein the PEG is PEG 2000.

In one embodiment, the method described above is provided, wherein the phospholipid added in step (3) is selected from the group consisting of soybean lecithin, hydrogenated soybean lecithin, dilauroyl lecithin, dimyristoyl lecithin, dipalmitoyl lecithin, distearoyl lecithin, 1-myristoyl-2-palmitoyl lecithin, 1-palmitoyl-2-myristoyl lecithin, 1-palmitoyl-2-stearoyl lecithin, 1-stearoyl-2-palmitoyl lecithin, yolk lecithin, dioleoyl lecithin, dilauroyl phosphatidylglycerol, dipalmitoyl phosphatidic acid, dimyristoyl phosphatidylethanolamine, dipalmitoyl phosphatidylethanolamine, dimyristoyl phosphatidyl serine, dipalmitoyl phosphatidyl di-serine, dipalmitoyl phosphatidylcholine, brain phosphatidyl serine, brain sphingomyelin, dipalmitoyl sphingomyelin, distearoyl sphingomyelin, distearoyl phosphatidylethanolamine (DSPE), or any combination thereof.

In one embodiment, the method described above is provided, wherein the molar ratio of c(RGD-ACP-K) to phospholipid-PEG-$R^1$ added in step (1) is 1:1.2, 1:1.5 or 1:2, preferably 1:1.2.

In one embodiment, the method described above is provided, wherein the phospholipid-PEG-$R^1$ is phospholipid-PEG-NHS.

In one embodiment, the method described above is provided, wherein the phospholipid-PEG is selected from the group consisting of distearoyl phosphatidylcholine-polyethylene glycol (PEG-DSPC), phosphatidylethanolamine-polyethylene glycol (PEG-PE), distearoyl phosphatidylethanolamine-polyethylene glycol (PEG-DSPE), phosphatidylcholine-polyethylene glycol (PEG-PC), more preferably distearoyl phosphatidylethanolamine-polyethylene glycol (PEG-DSPE).

In one embodiment, the method described above is provided, wherein in step (2), the moles of phospholipid-PEG-c(RGD-ACP-K) added account for 8%-12%, most preferably 8% of the moles of phospholipid-PEG added.

In a more specific embodiment, provided is a method for preparing the long-circulating liposome targeting tumors, comprising the steps of:
(1) Reacting c(RGD-ACP-K) with phospholipid-PEG-$R^1$ in the molar ratio of 1:1.2, terminating the reaction with glycine after c(RGD-ACP-K) is depleted, dialyzing the reaction, and then freeze-drying the reaction to give a lyophilizate, which is a mixture of phospholipid-PEG-c(RGD-ACP-K) and phospholipid-PEG in the molar ratio of 1:0.2, wherein $R^1$ is succinimidyl ester (-NHS);
(2) Preparing a blank long-circulating liposome from phospholipid, cholesterol, phospholipid-PEG, and the lyophilizate obtained in step (1), wherein the moles of phospholipid-PEG-c(RGD-ACP-K) added account for 4-16% (for example, 4%, 8%, 12% or 16%), more preferably 8%-12%, most preferably 8%, of the moles of phospholipid-PEG added;
(3) Incubating the blank long-circulating liposome obtained in step (2) with an anti-cancer agent solution, then passing the reaction through a dextran gel column, collecting the red liposome portion, and repeatedly extruding it through a 0.22 μm filter membrane, to give the long-circulating liposome modified with c(RGD-ACP-K),
wherein the anti-cancer agent is doxorubicin or a pharmaceutically acceptable salt thereof, such as doxorubicin hydrochloride, and
wherein the phospholipid-PEG is DSPE-PEG, preferably wherein the PEG is PEG2000.

In one embodiment, the method described above is provided, wherein the dextran gel column in step (3) is Sephadex G50 column, which is eluted with PBS buffer pH 7.4.

In one embodiment, the method described above is provided, wherein the filter membrane in step (3) is polycarbonate filter membrane.

In one embodiment, the method described above is provided, wherein in step (2), the ratio of phospholipid, cholesterol and phospholipid-PEG added is 3:1:1 by weight, and the moles of phospholipid-PEG-c(RGD-ACP-K) added account for 8% of the moles of phospholipid-PEG added.

In one embodiment, the method described above is provided, wherein the dialysis in step (1) is carried out with a dialysis bag having a molecular weight cutoff of 1000 Daltons.

In another aspect, the invention provides a long-circulating liposome modified with c(RGD-ACP-K) obtained by the method described above.

In another aspect, the invention provides a method for treating cancer, comprising administering a therapeutically effective amount of a long-circulating liposome modified with c(RGD-ACP-K) in accordance with the invention to a cancer patient. Said cancer is, for example, acute leukemia, such as lymphocytic leukemia and granulocytic leukemia; malignant lymphoma; breast cancer; lung cancer, such as small cell lung cancer, non-small cell lung cancer, bronchogenic carcinoma; ovarian cancer; soft tissue sarcoma; osteoblastic sarcoma; rhabdomyosarcoma; Ewing's sarcoma; nephroblastoma; neuroblastoma; bladder cancer; thyroid cancer; prostate cancer; head and neck squamous carcinoma; testicular cancer; stomach cancer; liver cancer; or melanoma, and the like.

In another aspect, the invention provides use of the long-circulating liposome modified with c(RGD-ACP-K) in accordance with the invention in the manufacture of an anti-cancer medicament.

In one embodiment, the medicament may be an injection, such as aqueous injection solution, lyophilized powder, or infusion, and the like.

In another aspect, provided is the long-circulating liposome modified with c(RGD-ACP-K) in accordance with the invention for use as a medicament.

In another aspect, the invention provides the long-circulating liposome modified with c(RGD-ACP-K) in accordance with the invention for use in the treatment of cancer, for example, acute leukemia, such as lymphocytic leukemia and granulocytic leukemia; malignant lymphoma; breast cancer; lung cancer, such as small cell lung cancer, non-small cell lung cancer, bronchogenic carcinoma; ovarian cancer; soft tissue sarcoma; osteoblastic sarcoma; rhabdomyosarcoma; Ewing's sarcoma; nephroblastoma; neuroblastoma; bladder cancer; thyroid cancer; prostate cancer; head and neck squamous carcinoma; testicular cancer; stomach cancer; liver cancer; or melanoma, and the like.

In another aspect, provided is the long-circulating liposome modified with c(RGD-ACP-K) in accordance with the invention, in form of injection, for example aqueous injection solution, lyophilized powder, or infusion, and the like.

The long-circulating liposome modified with c(RGD-ACP-K) in accordance with the invention or the anti-cancer medicament prepared therefrom can be used for the treatment of cancer, for example, acute leukemia, such as lymphocytic leukemia and granulocytic leukemia; malignant lymphoma; breast cancer; lung cancer, such as small cell lung cancer, non-small cell lung cancer, bronchogenic carcinoma; ovarian cancer; soft tissue sarcoma; osteoblastic sarcoma; rhabdomyosarcoma; Ewing's sarcoma; nephroblastoma; neuroblastoma; bladder cancer; thyroid cancer;

prostate cancer; head and neck squamous carcinoma; testicular cancer; stomach cancer; liver cancer; or melanoma, and the like.

The long-circulating liposome modified with c(RGD-ACP-K) in accordance with the invention may be administered in a therapeutically effective amount. A suitable dosage range is typically from 0.1 to 1000 mg·m$^{-2}$, preferably from 1 to 100 mg·m$^{-2}$, most preferably from 10 to 50 mg·m$^{-2}$, depending on factors such as the severity of the disease to be treated, the age and relative health of the individual, the indications against which the administration is carried out, and the experience of the medical practitioner involved. If desired, it may be lower or higher than the above dosage range. Any artisans with ordinary skill in the art in the cancer therapy field can determine the therapeutically effective amount of the active compound in the invention for a given disease without undue experimentation, relying on personal knowledge and the disclosure of this application.

As used herein, the term "therapeutically effective amount" means an amount sufficient to cause amelioration or healing of a disease in the subject. The "therapeutically effective amount" will vary depending on the used compound, the disease to be treated, the severity of the disease to be treated, the age and health status of the subject, the judgment of the attending physician or veterinary practitioner, and other factors.

As described above, the long-circulating liposome modified with c(RGD-ACP-K) in accordance with the invention has many advantages, and the target molecule c(RGD-ACP-K) used in the invention has a low molecular weight, causing lower antigenicity and less ease for immune response. The preparation method in accordance with the invention uses mild conditions, has rapid reaction, simple coupling of target molecule and mature procedures, and is suitable for scale industrial production.

In another aspect, the invention provides use of c(RGD-ACP-K) for the preparation of a liposome, preferably the invention provides use of c(RGD-ACP-K) for the preparation of a liposome comprising an anti-cancer agent, in particular doxorubicin or a pharmaceutically acceptable salt thereof, such as doxorubicin hydrochloride.

DESCRIPTION OF DRAWINGS

In FIGS. 1A, 1B and 1C, the symbol*represents that ANOVA showed a significant difference, p<0.05; the symbol**represents that ANOVA showed a very significant difference, p<0.01.

In FIG. 2, the symbol**represents that ANOVA showed a very significant difference, p<0.01. The phrase "target density" in FIG. 2 refers to the percent molar ratio of DSPE-PEG2000-c(RGD-ACP-K) to DSPE-PEG2000 added in the preparation of the liposomes.

In FIGS. 4A and 4B, the symbol*represents that ANOVA showed a significant difference, $p<0.05$; the symbol**represents that ANOVA showed a very significant difference, $p<0.01$.

EXAMPLES

The following examples are intended to further illustrate the invention, but shall not be construed as limitation to the invention.

Abbreviations:
PBS phosphate buffer solution
PEG polyethylene glycol
RGD arginine-glycine-asparate
PE-PEG phosphatidylethanolamine-polyethylene glycol
PC-PEG phosphatidylcholine-polyethylene glycol
DSPE-PEG distearoyl phosphatidylethanolamine-polyethylene glycol
DSPE-PEG-NHS distearoyl phosphatidylethanolamine-polyethylene glycol-N-hydroxysuccinamide
DSPE-PEG-BTA distearoylphosphatidylethanolamine-polyethylene glycol-benzotriazole
DSPE-PEG-c(RADfk) distearoyl phosphatidylethanolamine-polyethylene glycol-c(RADfk)
DSPE-PEG-c(RGD-ACP-K) distearoyl phosphatidylethanolamine-polyethylene glycol-c(RGD-ACP-K)
DSPE-PEG-ABHT distearoyl phosphatidylethanolamine-polyethylene glycol-ABHT
DSPE-PEG-c(RGD-AAB-K) distearoyl phosphatidylethanolamine-polyethylene glycol-c(RGD-AAB-K)
Neg-lipo doxorubicin hydrochloride loaded passively targeting long-circulating liposome modified only with PEG, but not modified with a cyclic peptide
c(RGDfk)-lipo doxorubicin hydrochloride loaded long-circulating liposome modified with c(RGDfk)
c(RADfk)-lipo doxorubicin hydrochloride loaded long-circulating liposome modified with c(RADfk)
ABHT-lipo doxorubicin hydrochloride loaded long-circulating liposome modified with ABHT
c(RGD-AAB-K)-lipo doxorubicin hydrochloride loaded long-circulating liposome modified with c(RGD-AAB-K)
c(RGD-ACP-K)-lipo doxorubicin hydrochloride loaded long-circulating liposome modified with c(RGD-ACP-K)

If not otherwise specified, the starting materials used for synthesis in the examples are all known in the art, and may be synthesized by a known method or are commercially available.

Example 1

Study on Different Molar Ratios of DSPE-PEG-NHS to c(RGD-ACP-K) in the Preparation of DSPE-PEG-c(RGD-ACP-K)

DSPE-PEG2000-NHS and the target molecule c(RGD-ACP-K) were separately dissolved in anhydrous dimethylformamide. The obtained solution of the target molecule c(RGD-ACP-K) had a concentration of 0.01 M, and the obtained solutions of DSPE-PEG2000-NHS had a concentration of 0.010 M, 0.012 M, 0.015 M, and 0.020 M, respectively. The same volume of the two solutions were added into a round bottom flask (so that the molar ratio of the target molecule c(RGD-ACP-K) to DSPE-PEG2000-NHS is 1:1, 1:1.2, 1:1.5 and 1:2), and was adjusted to pH 8-9 with triethylamine. The mixture was allowed to react at 4° C. for 4-10 hours, during which period the reaction was monitored with HPLC (Agilent high performance liquid chromatograph, model: Agilent 1260 LC; conditions: A: 0.1% aqueous solution of triethylamine; B: acetonitrile and water containing 0.1% triethylamine (80:20), B: 10%-35% gradient, 20 min).

The experimental results showed that the peak of the target molecule did not completely disappear in the end when the molar ratio of c(RGD-ACP-K) to DSPE-PEG2000-NHS was 1:1, but completely disappeared at the other three ratios, indicating that the target molecule completely reacted at all the three ratios of 1:1.2, 1:1.5, and 1:2, to replace NHS to form DSPE-PEG2000-c(RGD-ACP-K). Accordingly, the molar ratios of DSPE-PEG2000-c(RGD-ACP-K) to DSPE-PEG2000-NHS were 1:0.2, 1:0.5, and 1:1, respectively, at the end of the completion of the reaction. This also indicated that in the reaction to prepare the conjugate, the excess of DSPE-PEG-NHS facilitated the complete reaction.

Example 2

Preparation of DSPE-PEG-c(RADfk), DSPE-PEG-c(RGDfk), DSPE-PEG-ABHT, DSPE-PEG-c(RGD-AAB-K), DSPE-PEG-c(RGD-ACP-K)

DSPE-PEG2000-NHS and the target molecule c(RADfk), c(RGDfk), ABHT, c(RGD-AAB-K) or c(RGD-ACP-K) were separately dissolved in anhydrous dimethylformamide. The obtained solution of DSPE-PEG2000-NHS had a concentration of 0.012 M, and the obtained solution of the target molecule c(RADfk), c(RGDfk), ABHT, c(RGD-AAB-K) or c(RGD-ACP-K) had a concentration of 0.01 M. The two solutions were added to a round bottom flask (at the 1:1.2 molar ratio of the target molecule to DSPE-PEG2000-NHS), and was adjusted to pH 8-9 with triethylamine. The mixture was allowed to react at 4° C. for 4-10 hours, during which period the reaction was monitored with HPLC (Agilent high performance liquid chromatograph, model: Agilent 1260 LC; conditions: A: 0.1% aqueous solution of triethylamine; B: acetonitrile and water containing 0.1% triethylamine (80:20), B: 10%-35% gradient, 20 min) until the peak of the target molecule completely disappeared. After the reaction continued for another 12 hours, the reaction was terminated by adding excessive glycine. The reaction was then placed in a dialysis bag (MW=1000) and dialyzed against distilled water for 48 hours. The dialyzed liquid was lyophilized for use. The freeze-drying conditions were as follows:

Pre-freezing: −45° C., 300 min;
Primary drying: stage 1 (−40° C.): 600 min
  stage 2 (−30° C.): 600 min
  stage 3 (−20° C.): 360 min
  stage 4 (−10° C.): 360 min Secondary drying: stage 1 (10° C.): 60 min
   stage 2 (20° C.): 60 min
   stage 3 (25° C.): 120 min The obtained lyophilizates were a mixture of DSPE-PEG2000-c(RADfk), DSPE-PEG2000-c(RGDfk), DSPE-PEG2000-ABHT, DSPE-PEG2000-c(RGD-AAB-K) or DSPE-PEG2000-c(RGD-ACP-K) to DSPE-PEG2000-NHS in the molar ratio of 1:0.2, respectively.

The matrix-assisted laser desorption/ionization time-of-flight mass spectrometry (MALDI-TOF-MS) (model: microflex, manufacturer: Bruker, USA) was used to analyze the molecular weight of the product contained in the dialyzed liquid. The results showed that there was a peak with normal distribution at the molecular weight of 3500, which proved that the products DSPE-PEG2000-c(RADfk), DSPE-PEG2000-c(RGDfk), DSPE-PEG2000-ABHT, DSPE-PEG2000-c(RGD-AAB-K), DSPE-PEG2000-c(RGD-ACP-K) were indeed synthesized.

Example 3

Preparation of Doxorubicin Hydrochloride Loaded Long-Circulating Liposomes Modified with c(RADfk), c(RGDfk), ABHT, c(RGD-AAB-K), c(RGD-ACP-K) and Doxorubicin Hydrochloride Loaded Passively Targeted Long-Circulating Liposome Hydrogenated soybean lecithin, cholesterol and DSPE-PEG2000 (weight ratio of the three components=3:1:1) as well as the lyophilizate prepared in Example 2 (the moles of DSPE-PEG2000-c(RADfk), DSPE-PEG2000-c(RGDfk), DSPE-PEG2000-ABHT, DSPE-PEG2000-c(RGD-AAB) or DSPE-PEG2000-c(RGD-ACP-K) added account for 8% of the moles of DSPE-PEG2000 added) were charged into a round bottom flask, dissolved in chloroform, and evaporated on a rotary evaporator at 37° C. for 30 min to remove the organic solvent to give a uniform and transparent thin film. The thin film was placed in a vacuum oven overnight to remove residual organic solvent. An appropriate amount of aqueous ammonium sulfate solution (123 mM, pH 5.4) was added. The mass was vortexed for a short time followed by ultrasonication with a probe until a blue opalescence appeared. The reaction was passed through Sephadex G50 column, which was eluted with PBS buffer (pH=7.4). The liposome fraction was collected to obtain a blank long-circulating liposome modified with c(RADfk), c(RGDfk), ABHT, c(RGD-AAB-K), or c(RGD-ACP-K).

The blank passively targeted long-circulating liposome was prepared only using hydrogenated soybean lecithin, cholesterol, DSPE-PEG2000 according to the procedure above.

The collected blank long-circulating liposomes were incubated with doxorubicin hydrochloride stock solution (aqueous solution, 5 mg/ml) at 60° C. for 20 min under shaking. The reaction was passed through Sephadex G50 column, which was eluted with PBS buffer (pH=7.4). The red liposome fraction was collected and repeatedly extruded through 0.22 μm polycarbonate filter membrane to give the title product. The obtained doxorubicin hydrochloride loaded long-circulating liposomes modified with c(RADfk), c(RGDfk), ABHT, c(RGD-AAB-K), c(RGD-ACP-K) are referred to as c(RADfk)-lipo, c(RGDfk)-lipo, ABHT-lipo, c(RGD-AAB-K)-lipo, c(RGD-ACP-K)-lipo, respectively, and the obtained doxorubicin hydrochloride loaded passively targeted long-circulating liposome is referred to as Neg-lipo.

Example 4

Study on Physicochemical Properties of Doxorubicin Hydrochloride Loaded Long-Circulating Liposomes Modified with c(RADfk), c(RGDfk), ABHT, c(RGD-AAB-K), c(RGD-ACP-K) and Doxorubicin Hydrochloride Loaded Passively Targeted Long-Circulating Liposome The physicochemical properties of various long-circulating liposomes prepared in Example 3 were determined using Malvern particle size analyzer (MS2000MU) (instrument model: Nano ZS; conditions: dispersion medium: water; sample cell: PCS1115; temperature: 25° C.; number of determination: 3 times), including particle size, particle size distribution, polydispersity index (PDI), and surface potential.

The encapsulation efficiency and release of doxorubicin hydrochloride were determined by ultraviolet spectrophotometer (Beijing Purkinje General, T6 New Century). The release method was as follows: an equal volume of various long-circulating liposomes prepared in Example 3 and serum-containing medium were placed in a dialysis bag (MW=14000) with PBS (pH=7.4) as the release medium. After 48 hours, a sample (5 ml) was taken for the determination of the concentration of the active agent by an ultraviolet spectrophotometer (Beijing Purkinje General, T6 New Century, detection wavelength: 485 nm), and the cumulative release rate was calculated.

At the same time, in order to verify the reliability of the release method, the same release method was carried out with an equal concentration of free doxorubicin hydrochloride, and the results showed almost all doxorubicin hydrochloride was released within 48 hours, which indicated that the release method used in this example was reliable, and was capable of showing the release profile of doxorubicin hydrochloride from the liposomes.

TABLE 1

| Preparation | Average Particle Size (nm) | PDI | Potential (mV) | Encapsulation efficiency (%) | Release rate (48 h, %) |
| --- | --- | --- | --- | --- | --- |
| Neg-lipo | 98.32 | 0.08 | −4.45 | 90.26% | 3.68 |
| c(RADfk)-lipo | 105.87 | 0.22 | −0.25 | 89.29% | 5.58 |
| c(RGDfk)-lipo | 100.69 | 0.11 | −1.49 | 88.85% | 4.69 |
| ABHT-lipo | 86.24 | 0.13 | 0.17 | 96.32% | 2.55 |
| c(RGD-AAB-K)-lipo | 95.63 | 0.18 | −1.23 | 99.02% | 4.96 |
| c(RGD-ACP-K)-lipo | 101.47 | 0.20 | −0.50 | 93.81% | 4.70 |

Notes:
the release rate of free doxorubicin hydrochloride in 48 hours was 98.34%.

Example 5

Figure 1A:
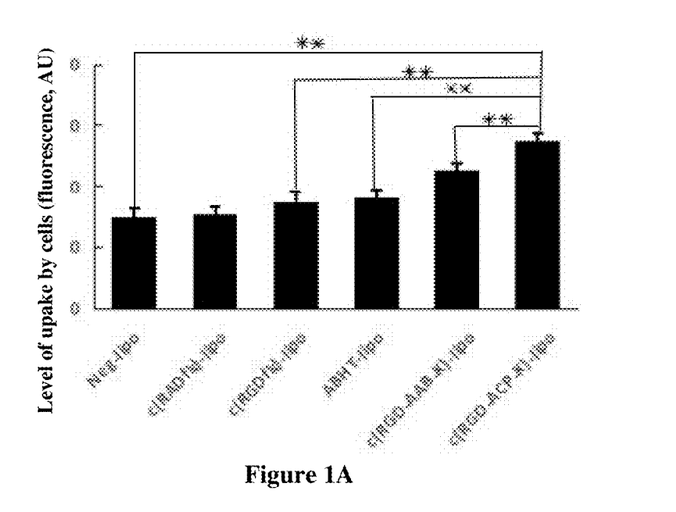
FIGS. 1A, 1B and 1C show the in vitro cell targeting of the long-circulating liposomes modified with DSPE-PEG-c(RADfk), DSPE-PEG-c(RGDfk), DSPE-PEG-ABHT, DSPE-PEG-c(RGD-AAB-K) and DSPE-PEG-c(RGD-ACP-K) (represented by c(RADfk)-lipo, c(RGDfk)-lipo, ABHT-lipo, c(RGD-AAB-K)-lipo and c(RGD-ACP-K)-lipo, respectively) as well as passively targeted long-circulating liposomes (Neg-lipo), as examined in high content experiment (High Content Analyzer, PerkinElmer, USA). The results showed that the long-circulating liposomes tested in melanoma B16 cells (FIG. 1A), human umbilical vein endothelial cells (HUVEC cells) (FIG. 1B) and breast cancer cells (MCF7 cells) (FIG. 1C) had targeting in the order from high to low: c(RGD-ACP-K)-lipo>c(RGD-AAB-K)-lipo>ABHT-lipo>c(RGDfk)-lipo>c(RADfk)-lipo>Neg-lipo, and the targeting of c(RGD-ACP-K)-lipo was significantly higher than that of all other liposomes. Among the three cells used, B16 cells and HUVEC cells exhibit high expression of integrin $\alpha_v\beta_3$, and MCF7 cells exhibit low expression of integrin $\alpha_v\beta_3$. It was seen from the experimental results that all three types of cells highly specifically uptook c(RGD-ACP-K)-lipo, indicating c(RGD-ACP-K)-lipo not only targeted cells with high expression of integrin $\alpha_v\beta_3$, but also cells with low expression of integrin $\alpha_v\beta_3$.
Figure 1B:
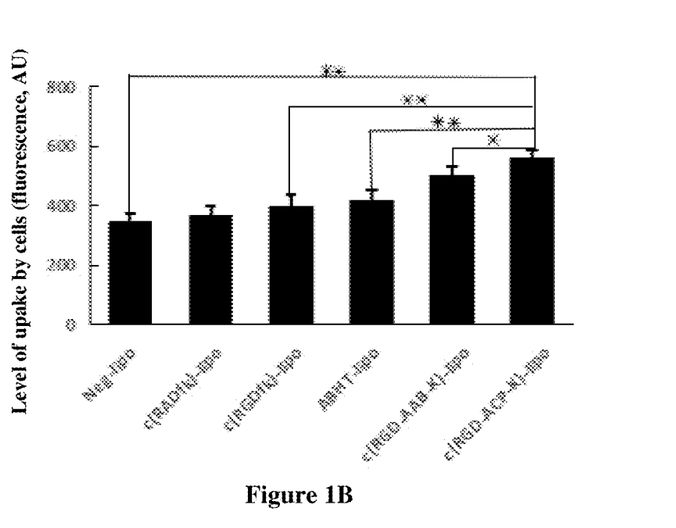
Figure 1C:
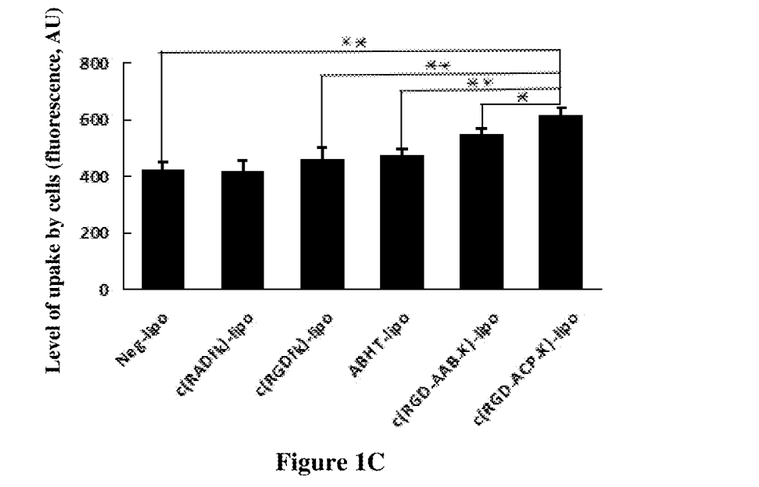

In Vitro Targeting Study on Doxorubicin Hydrochloride Loaded Long-Circulating Liposome Modified with c(RADfk), c(RGDfk), ABHT, c(RGD-AAB-K), or c(RGD-ACP-K) and Doxorubicin Hydrochloride Loaded Passively Targeted Long-Circulating Liposome The in vitro cell targeting of the prepared long-circulating liposomes was examined using high content experiment (High Content Analyzer, PerkinElmer, USA). The various long-circulating liposomes prepared in Example 3 were incubated at the same concentration (300 ng/ml) with B16 cells, HUVEC cells or MCF7 cells at 37° C. for 2 hours. Then, the cells were fixed with 4% paraformaldehyde at 37° C. for 20 min, and finally were stained on the nuclei by Hochest 33258. The uptake of the liposomes by the cells was quantified using High Content Analyzer (PerkinElmer, USA). The measured fluorescence value was directly proportional to the uptake of the liposomes by the cells, reflecting the level of uptake of the liposomes by the cells. The experimental results are shown in FIGS. 1A, 1B and 1C.

The results of the measured fluorescence values showed that in B16 cell model (FIG. 1A), HUVEC cell model (FIG. 1B) and MCF7 cell model (FIG. 1C), the level of uptake of the examined long-circulating liposomes by the three cells, namely, the targeting of the examined long-circulating liposomes to the three cells, was in the order from high to low: c(RGD-ACP-K)-lipo>c(RGD-AAB-K)-lipo>ABHT-Lipo>c(RGDfk)-lipo>c(RADfk)-lipo>Neg-lipo. The statistic analysis showed that the targeting of c(RGD-ACP-K)-lipo was significantly higher than that of all other liposomes (p<0.05 or p<0.01). Among the three cells used, B16 cells and HUVEC cells exhibit high integrin $\alpha_v\beta_3$ expression, and MCF7 cells exhibit low integrin $\alpha_v\beta_3$ expression. It can be seen from the experimental results that all three cells uptook c(RGD-ACP-K)-lipo with high selectivity, which indicated that c(RGD-ACP-K)-lipo targeted not only cells with high expression of the receptor integrin $\alpha_v\beta_3$, but also cells with low expression of the receptor integrin $\alpha_v\beta_3$. The mechanism of targeting of c(RGD-ACP-K)-lipo to tumors is not limited to being selectively recognized by the receptor integrin $\alpha_v\beta_3$, and there are still other unknown mechanisms leading to its ability to target tumor cells with low expression of the receptor integrin $\alpha_v\beta_3$ and the uptake by such tumor cells. It is shown that the liposome modified with c(RGD-ACP-K) as carrier of an anti-cancer agent can be applied to more variety of cancers, and has a wider range of applications.

Example 6

Figure 2:
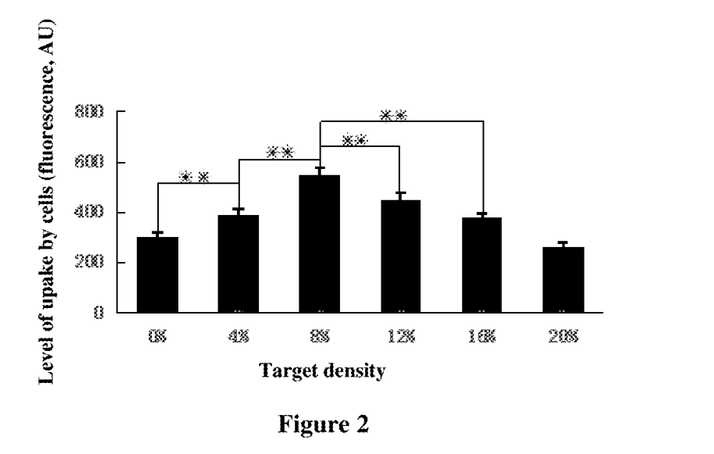
FIG. 2 shows the effect of the preparation of the long-circulating liposomes using different amounts of phospholipid-PEG-c(RGD-ACP-K) and phospholipid-PEG on the in vitro cell targeting of the obtained liposomes, as examined in high content experiment (High Content Analyzer, PerkinElmer, USA). The results showed that in the B16 cell model, the different amounts of phospholipid-PEG-c(RGD-ACP-K) and phospholipid-PEG used to prepare the doxorubicin hydrochloride loaded long-circulating liposomes had a significant effect on the in vitro cell targeting of the obtained liposomes. In the range from 0 to 20% phospholipid-PEG-c(RGD-ACP-K)/phospholipid-PEG molar ratio examined, the doxorubicin hydrochloride loaded long-circulating liposomes modified with c(RGD-ACP-K) had in vitro cell targeting in the order from high to low: 8%>12%>4%>16%>0%>20%. The in vitro cell targeting was better in the range from 4% to 16% phospholipid-PEG-c(RGD-ACP-K)/phospholipid-PEG molar ratio, and even better in the range from 8% to 12% phospholipid-PEG-c(RGD-ACP-K)/phospholipid-PEG molar ratio, and the best at the 8% phospholipid-PEG-c(RGD-ACP-K)/phospholipid-PEG molar ratio. When the phospholipid-PEG-c(RGD-ACP-K)/phospholipid-PEG molar ratio rose to 20%, the uptake of the liposome modified with c(RGD-ACP-K) by the cells was less than that of the liposome without the modification.

Effect of Different Amounts of DSPE-PEG2000-c(RGD-ACP-K) and DSPE-PEG2000 on the In Vitro Cell Targeting of Long-Circulating Liposomes The effect of different molar ratios of DSPE-PEG2000-c(RGD-ACP-K) to DSPE-PEG2000 on the in vitro cell targeting of the long-circulating liposomes was investigated using high content experiment (High Content Analyzer, PerkinElmer, USA). Doxorubicin hydrochloride loaded long circulating liposomes were prepared according to the method of Example 3 using the molar ratio DSPE-PEG2000-c(RGD-ACP-K) to DSPE-PEG2000 of 0%, 4%, 8%, 12%, 16% and 20%. The prepared liposomes were incubated with B16 cells at 37° C. for 2 hours at the same concentration (300 ng/ml). Then, the cells were fixed with 4% paraformaldehyde at 37° C. for 20 min, and finally were stained on the nuclei with Hochest 33258. The uptake of the liposomes by the cells was quantified using the High Content Analyzer. The measured fluorescence value was directly proportional to the uptake of the liposomes by the cells, reflecting the level of uptake of the liposomes by the cells. The experimental results are shown in FIG. 2.

The results of the measured fluorescence values showed that the use of different DSPE-PEG2000-c(RGD-ACP-K)/DSPE-PEG2000 molar ratios in the preparation of the long-circulating liposomes had significant influence on the in vitro cell targeting of the long-circulating liposomes in the B16 cell model. In the range from 0 to 20% of the DSPE-PEG2000-c(RGD-ACP-K)/DSPE-PEG2000 molar ratios investigated, the in vitro cell targeting of the long-circulating liposomes was in the order from high to low: 8%>12%>4%>16%>0%>20%. The in vitro cell targeting of the long-circulating liposomes was better in the range from 4% to 16% DSPE-PEG2000-c(RGD-ACP-K)/DSPE-PEG2000 molar ratio, and even better in the range from 8% to 12% DSPE-PEG2000-c(RGD-ACP-K)/DSPE-PEG2000 molar ratio, and the best at the 8% DSPE-PEG2000-c(RGD-ACP-K)/DSPE-PEG2000 molar ratio. When the DSPE-PEG2000-c(RGD-ACP-K)/DSPE-PEG2000 molar ratio rose to 20%, the uptake of the liposomes modified with c(RGD-ACP-K) by the cells was less than that of the liposomes without the modification. The inventors also investigated the targeting of the long-circulating liposome prepared in the DSPE-PEG2000-c(RGD-ACP-K)/DSPE-PEG2000 molar ratio of 40% according to the same method, and found that the uptake of the liposome by the cells was quite undesirable. Therefore, the ratio of DSPE-PEG2000-c(RGD-ACP-K)/DSPE-PEG2000 should not be too high.

Example 7

Pharmacodynamic Study of the Doxorubicin Hydrochloride Loaded Long-Circulating Liposome Modified with c(RGD-ACP-K)

Control: PBS buffer (pH=7.4) and doxorubicin hydrochloride loaded passively targeted long-circulating liposome (Neg-lipo).

Reference preparations: doxorubicin hydrochloride loaded long-circulating liposomes modified with the cyclic peptides c(RGDfk) (c(RGDfk)-lipo) and c(RADfk) (c(RADfk)-lipo)

Test preparations: ABHT-lipo, c(RGD-AAB-K)-lipo and c(RGD-ACP-K)-lipo

The liposomes above were prepared as described in Example 3.

Experimental animals: C57BL/6 mice (body weight 18-22 g, male) inoculated with murine melanoma B16 were divided into five groups, each consisting of 7 to 9 mice. After twelve days from the inoculation, the mice were administered via the tail vein with 2 mg of doxorubicin hydrochloride/kg body weight from Day 13, once every other day for a total of four times. The tumor volume and the final tumor weight at the end of the experiment were measured as parameters indicating the tumor growth. The tumor volume was measured every other day. Finally, the mice were sacrificed by cervical dislocation, and the melanoma of the mice was collected, photographed and weighted.

Figure 3A:
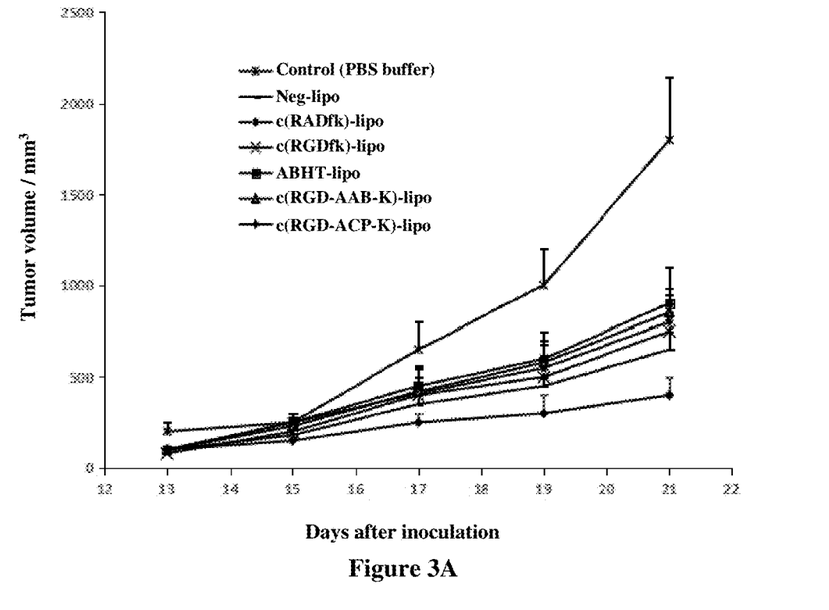
FIGS. 3A and 3B show the tumor volume curves in mice after administration via the tail vein injection of doxorubicin hydrochloride loaded passively targeting liposome (Neg-lipo) as well as the doxorubicin hydrochloride loaded actively targeting liposomes (c(RADfk)-lipo, c(RGDfk)-lipo, ABHT-lipo, c(RGD-AAB-K)-lipo, c(RGD-ACP-K)-lipo). The curves in FIG. 3A represent c(RGD-ACP-K)-lipo, Neg-lipo, c(RGDfk)-lipo, c(RADfk)-lipo, c(RGD-AAB-K)-lipo, ABHT-lipo and the control (PBS buffer) from the bottom to the top, respectively. It was seen from FIG. 3A that as far as the tumor suppressive effect as evaluated by tumor volume, the order of tumor suppressive effect of these liposomes from high to low was as follows: c(RGD-ACP-K)-lipo>Neg-lipo>c(RGDfk)-lipo, c(RADfk)-lipo>c(RGD-AAB-K)-lipo>ABHT-lipo>control (PBS buffer). The curves in FIG. 3B represent c(RGD-ACP-K)-lipo, Neg-lipo, c(RGDfk)-lipo and the control (PBS buffer) from the bottom to the top, respectively. As seen from FIG. 3B, ANOVA showed that there was a significant difference between c(RGD-ACP-K)-lipo and Neg-lipo on Day 7 after the administration (p<0.05), and between c(RGD-ACP-K)-lipo and c(RGDfk)-lipo on Day 9 after administration (p<0.05). The c(RGD-ACP-K)-lipo group showed the best tumor suppressive effect, which was better than that of the positive control group c(RGDfk)-lipo. The symbol*in FIGS. 3A and 3B represents that ANOVA showed a significant difference, p<0.05.
Figure 3B:
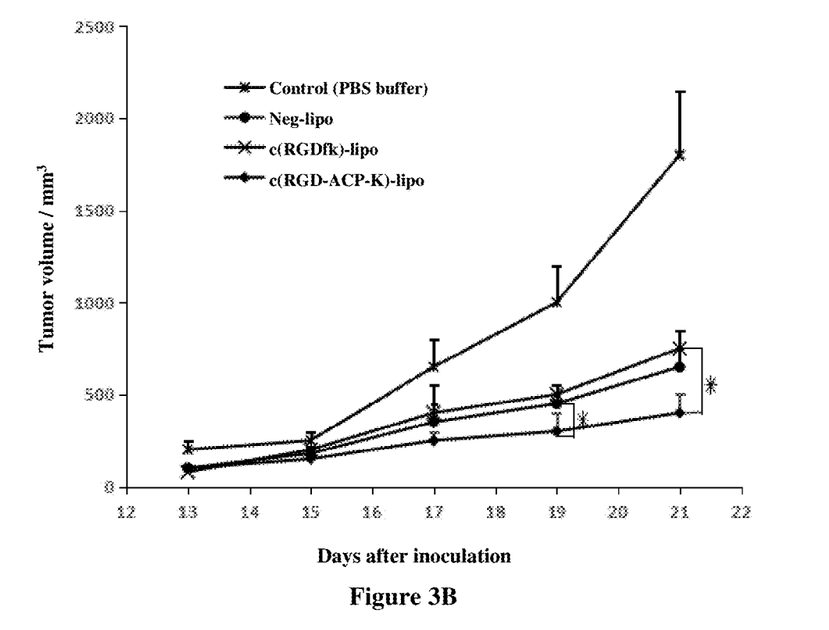
Figure 4A:
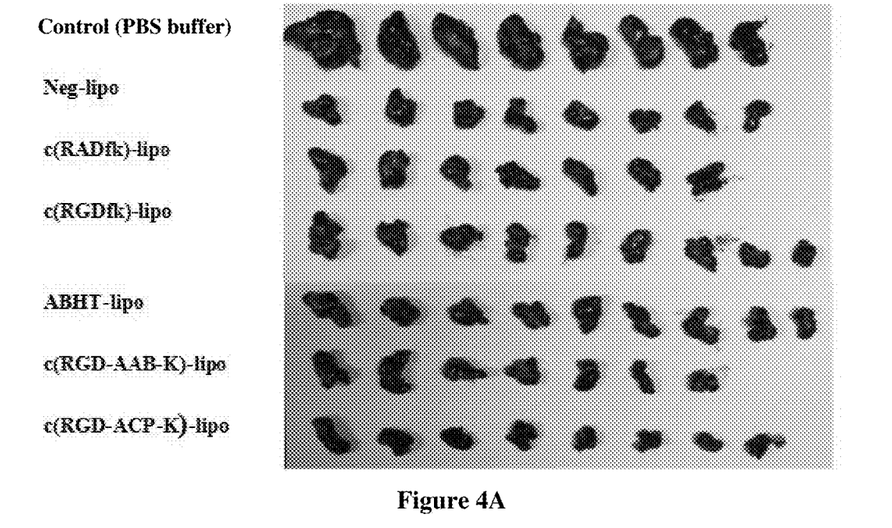
FIGS. 4A and 4B show the photos indicating the final volume of the tumors and the final weight of the tumors in mice, respectively, at the end of experiments by administering via the tail vein injection of doxorubicin hydrochloride loaded passively targeting liposome (Neg-lipo) as well as various doxorubicin hydrochloride loaded actively targeting liposomes (c(RADfk)-lipo, c(RGDfk)-lipo, ABHT-lipo, c(RGD-AAB-K)-lipo, c(RGD-ACP-K)-lipo). As seen from FIGS. 4A and 4B, the order of tumor suppressive effect of these liposomes from high to low was as follows: c(RGD-ACP-K)-lipo>c(RGD-AAB-K)-lipo>Neg-lipo>c(RGDfk)-lipo≈c(RADfk)-lipo>ABHT-lipo>the control (PBS buffer). The tumor suppressive effects of all treated groups were very significantly different from that of the control, PBS buffer (ANOVA, $p<0.01$). The tumor suppressive effect of the group treated with c(RGD-ACP-K)-lipo was significantly different from that of the group treated with c(RGD-AAB-K)-lipo (ANOVA, $p<0.05$), and very significantly different from that of the groups treated with Neg-lipo, c(RGDfk)-lipo, c(RADfk)-lipo and ABHT-lipo (ANOVA, $p<0.01$). That is, the tumor weight of the group treated with c(RGD-ACP-K)-lipo was significantly less than that of all other groups at the end of the experiment.
Figure 4B:
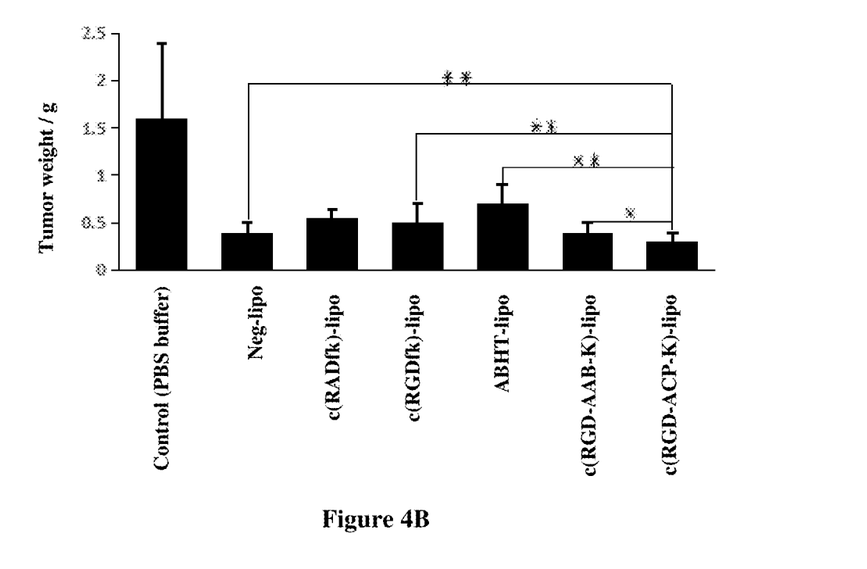

Experimental results: the changes of tumor volume in mice are shown in FIGS. 3A and 3B, and the tumor photographs and tumor weights after the mice were sacrificed are shown in FIGS. 4A and 4B.

FIGS. 3A and 3B show that the curves of the tumor volume in mice after the administration via tail vein injection of doxorubicin hydrochloride loaded passively targeted liposomes (Neg-lipo) and various doxorubicin hydrochloride loaded actively targeting liposomes (c(RADfk)-lipo, c(RGDfk)-lipo, ABHT-lipo, c(RGD-AAB-K)-lipo, c(RGD-ACP-K)-lipo). The curves from the bottom to the top in FIG. 3A represent the results of c(RGD-ACP-K)-lipo, Neg-lipo, c(RGDfk)-lipo, c(RADfk)-lipo, c(RGD-AAB-K)-lipo, ABHT-lipo and the control (PBS buffer), respectively. As can be seen from FIG. 3A, in terms of the tumor suppressive effect indicated by tumor volume, the order of tumor suppressive effect of various liposomes from high to low was as follows: c(RGD-ACP-K)-lipo>Neg-lipo>c(RGDfk)-lipo, c(RADfk)-lipo>c(RGD-AAB-K)-lipo>ABHT-lipo>the control (PBS buffer). The curves in FIG. 3B from the bottom to the top represent the results of c(RGD-ACP-K)-lipo, Neg-lipo, c(RGDfk)-lipo and the control (PBS buffer), respectively. As can be seen from FIG. 3B, ANOVA showed that on Day 7 after the first administration (i.e., on the $19^{th}$ day of the experiment), c(RGD-ACP-K)-lipo showed a significant difference as compared with Neg-lipo ($p<0.05$); on Day 9 after the first administration (i.e., on the $21^{st}$ day of the experiment), c(RGD-ACP-K)-lipo showed a significant difference as compared with c(RGDfk)-lipo ($p<0.05$). The c(RGD-ACP-K)-lipo group showed the best tumor suppressive effect, which was better than that of the positive control c(RGDfk)-lipo. The symbol*in FIGS. 3A and 3B represents that ANOVA showed a significant difference, $p<0.05$.

FIGS. 4A and 4B show the photos indicating the final tumor volumes and the final tumor weights in the mice, respectively, at the end of experiments by administering via the tail vein injection of doxorubicin hydrochloride loaded passively targeting liposome (Neg-lipo) and various doxorubicin hydrochloride loaded actively targeting liposomes (c(RADfk)-lipo, c(RGDfk)-lipo, ABHT-lipo, c(RGD-AAB-K)-lipo, c(RGD-ACP-K)-lipo). As seen from FIGS. 4A and 4B, the order of the tumor suppressive effect of these liposomes from high to low was as follows: c(RGD-ACP-K)-lipo>c(RGD-AAB-K)-lipo>Neg-lipo>c(RGDfk)-lipo≈c(RADfk)-lipo>ABHT-lipo>the control (PBS buffer). The tumor suppressive effects of all treated groups were very significantly different from that of the control, PBS buffer (ANOVA, $p<0.01$). The tumor suppressive effect of the group treated with c(RGD-ACP-K)-lipo was significantly different from that of the group treated with c(RGD-AAB-K)-lipo (ANOVA, $p<0.05$), and very significantly different from that of the group treated with Neg-lipo, c(RGDfk)-lipo, c(RADfk)-lipo, or ABHT-lipo (ANOVA, $p<0.01$). That is, the tumor weight of the group treated with c(RGD-ACP-K)-lipo was significantly less than that of all other groups at the end of the experiment. In FIGS. 4A and 4B, the symbol * represents that ANOVA showed a significant difference, $p<0.05$; the symbol ** represents that ANOVA showed a very significant difference, $p<0.01$.

The in vitro experimental results of FIGS. 1A, 1B and 1C showed that the doxorubicin hydrochloride loaded long-circulating liposomes modified with c(RGD-ACP-K) had the best targeting property, and the in vivo experimental results of FIGS. 3A, 3B, 4A and 4B also showed that the doxorubicin hydrochloride loaded long-circulating liposome modified with c(RGD-ACP-K) had the best anti-tumor effect, so the in vivo experimental results of the doxorubicin hydrochloride loaded long-circulating liposome modified with c(RGD-ACP-K) was consistent with the in vitro experimental results thereof.

Example 8

Evaluation on Cardiotoxicity of Doxorubicin Hydrochloride Loaded Long-circulating Liposome in Accordance with the Invention After the end of the pharmacodynamic test of Example 7, the hearts of the mice in each group were subjected to paraffin sectioning and then hematoxylin-eosin staining (HE staining) The damage to the myocardial cells of the mice in each group was observed under the microscope.

The results showed that the group treated with c(RGD-ACP-K)-lipo did not exhibit any cytonecrosis and had the lowest cardiotoxicity among all groups.

Example 9

Preparation of Cisplatin Loaded Long-Circulating Liposome Modified with c(RGD-ACP-K) and Pharmacodynamic Studies thereof Hydrogenated soybean lecithin, cholesterol, DSPE-PEG2000 and the lyophilizate prepared in Example 2 were charged into a round bottom flask (the weight ratio of hydrogenated soybean lecithin:cholesterol:DSPE-PEG2000=3:1:1, and the moles of DSPE-PEG2000-c(RGD-ACP-K) added accounted for 8% of the moles of DSPE-PEG2000 added), dissolved in chloroform, and evaporated on a rotary evaporator at 37° C. for 30 min to remove the organic solvent to give a uniform and transparent thin film. The thin film was placed in a vacuum oven overnight to remove residual organic solvent. An appropriate amount of aqueous solution was added. The mass was vortexed for a short time followed by ultrasonication with a probe until a blue opalescence appeared. The reaction was passed through Sephadex G50 column, eluted with PBS buffer (pH=7.4). The liposome fraction was collected to obtain a blank long-circulating liposome modified with c(RGD-ACP-K).

The blank passively targeted long-circulating delivery system was prepared only using hydrogenated soybean lecithin, cholesterol, DSPE-PEG2000 according to the procedure above.

The collected blank delivery systems were incubated with cisplatin stock solution (10 mg/ml in water) at 50° C. for 1 hour with shaking, respectively. The reaction systems were passed through Sephadex G50 column and eluted with PBS buffer (pH=7.4). The liposome fractions were collected and repeatedly extruded through a 0.22 μm polycarbonate filter membrane. Consequently, the title product was obtained with the encapsulation efficiency of 96% as determined. The cisplatin loaded liposome modified with c(RGD-ACP-K) is called c(RGD-ACP-K)-lipo-platin, and the cisplatin loaded long-circulating liposome prepared from the blank passively targeted delivery system is called Neg-lipo-platin.

Control: PBS solution (pH=7.4) and the passively targeted delivery system (Neg-lipo-platin).

Test preparation: c(RGD-ACP-K)-lipo-platin

Experimental animals: C57BL/6 mice (body weight 18-22 g, male) inoculated with murine melanoma B16 were divided into 5 groups, each consisting of 7 to 9 mice. After twelve days from the inoculation, the mice were administered via the tail vein with 5 mg of cisplatin/kg body weight, once every other day for a total of four times. The tumor volume and the final tumor weight at the end of the experiment were measured as parameters indicating the tumor growth. The tumor volume was measured every other day. Finally, the mice were sacrificed by cervical dislocation, and the tumors of the mice were collected and weighted.

The results showed that although the anti-tumor effect of c(RGD-ACP-K)-lipo-platin was significantly better than that of PBS (pH=7.4), but there was no statistically significant difference in tumor weight between c(RGD-ACP-K)-lipo-platin and Neg-lipo-platin.

While the invention has been described with reference to the specific embodiments thereof, it should be understood by those skilled in the art that various changes may be made and equivalents may be substituted without departing from the spirit and scope of the invention. All such equivalent technical solutions are intended to be within the scope of the claims appended hereto.

What is claimed:

1. A long-circulating liposome wherein the surface of the liposome is modified with c(RGD-ACP-K), which is linked to PEG via a chemical bond, and the PEG is linked to a phospholipid on the surface of the liposome, and wherein said liposome comprises an anticancer agent which is doxorubicin or a pharmaceutically acceptable salt thereof.

2. The long-circulating liposome according to claim 1, wherein said phospholipid is selected from the group consisting of distearoyl phosphatidylcholine (DSPC), phosphatidylethanolamine (PE), distearoyl phosphatidylethanolamine (DSPE), and phosphatidylcholine (PC).

3. The long-circulating liposome according to claim 1, wherein said anticancer agent is doxorubicin hydrochloride.

4. The long-circulating liposome according to claim 1, wherein said PEG has a molecular weight from 200 to 50000.

5. The long-circulating liposome according to claim 4, wherein said PEG is PEG 2000.

6. A method for preparing a long-circulating liposome modified with c(RGD-ACP-K), comprising the steps of:
   (1) Reacting excessive phospholipid-PEG-$R^1$ with c(RGD-ACP-K), terminating the reaction with glycine after c(RGD-ACP-K) is depleted, dialyzing the reaction, and then freeze-drying the reaction to give a lyophilizate, which is a mixture of phospholipid-PEG-c(RGD-ACP-K) and phospholipid-PEG-$R^1$, wherein $R^1$ is succinimidyl ester (-NHS) or benzotriazolyl (-BTC);
   (2) Preparing a blank long-circulating liposome from phospholipid, cholesterol, phospholipid-PEG, and the lyophilizate obtained in step (1), wherein the moles of phospholipid-PEG-c(RGD-ACP-K) added account for 4-16% of the moles of phospholipid-PEG added;
   (3) Incubating the blank long-circulating liposome obtained in step (2) with an anti-cancer agent solution, then passing the reaction through a dextran gel column, eluting and collecting the red liposome portion, and repeatedly extruding it through a 0.22 μm filter membrane, to give the anti-cancer agent loaded long-circulating liposome modified with c(RGD-ACP-K),
wherein said anti-cancer agent is doxorubicin or a pharmaceutically acceptable salt thereof.

7. The method according to claim 6, wherein said PEG has a molecular weight from 200 to 50000, and wherein the phospholipid added in step (2) is selected from the group consisting of soybean lecithin, hydrogenated soybean lecithin, dilauroyl lecithin, dimyristoyl lecithin, dipalmitoyl lecithin, distearoyl lecithin, 1-myristoyl-2-palmitoyl lecithin, 1-palmitoyl-2-myristoyl lecithin, 1-palmitoyl-2-stearoyl lecithin, 1-stearoyl-2-palmitoyl lecithin, yolk lecithin, dioleoyl lecithin, dilauroyl phosphatidylglycerol, dipalmitoyl phosphatidic acid, dimyristoyl phosphatidylethanolamine, dipalmitoyl phosphatidylethanolamine, dimyristoyl phosphatidyl serine, dipalmitoyl phosphatidyl di-serine, dipalmitoyl phosphatidyl choline, brain phosphatidyl serine, brain sphingomyelin, dipalmitoyl sphingomyelin, distearoyl sphingomyelin, distearoyl phosphatidylethanolamine (DSPE), and any combination thereof.

8. The method according to claim 6, wherein in step (1), c(RGD-ACP-K) and phospholipid-PEG-$R^1$ are added in the molar ratio of 1:1.2, 1:1.5 or 1:2, and wherein said phospholipid-PEG-$R^1$ is phospholipid-PEG-NHS.

9. The method according to claim 6, wherein said phospholipid-PEG added in step (2) is selected from the group consisting of distearoyl phosphatidylcholine-polyethylene glycol (PEG-DSPC), phosphatidylethanolamine-polyethylene glycol (PEG-PE), distearoyl phosphatidylethanolamine-polyethylene glycol (PEG-DSPE), or phosphatidylcholine-polyethylene glycol (PEG-PC).

10. The method according to claim 6, wherein in step (2), the moles of phospholipid-PEG-c(RGD-ACP-K) added account for 8-12%.

11. The method according to claim 6, comprising the steps of:
   (1) Reacting c(RGD-ACP-K) with DSPE-PEG200-$R^1$ in the molar ratio of 1:1.2, terminating the reaction with glycine after c(RGD-ACP-K) is depleted, dialyzing the reaction, and then freeze-drying the reaction to give a lyophilizate, which is a mixture of DSPE-PEG2000-c(RGD-ACP-K) and DSPE-PEG200-$R^1$ in the molar ratio of 1:0.2, wherein $R^1$ is succinimidyl ester (-NHS);
   (2) Preparing a blank long-circulating liposome from phospholipid, cholesterol, DSPE-PEG2000, and the lyophilizate obtained in step (1), wherein the moles of DSPE-PEG2000-c(RGD-ACP-K) added account for 4-16%, or 8%-12% of the moles of DSPE-PEG2000 added;
   (3) Incubating the blank long-circulating liposome obtained in step (2) with an anti-cancer agent solution, then passing the reaction through a dextran gel column, collecting the red liposome portion, and repeatedly extruding it through a 0.22 μm filter membrane, to give the long-circulating liposome modified with c(RGD-ACP-K),
wherein said anti-cancer agent is doxorubicin hydrochloride, and said phospholipid added in step (2) is hydrogenated soybean lecithin.

12. The method according to claim 11, wherein in step (3), the dextran gel column is Sephadex G50 column, which is eluted with PBS buffer, pH 7.4, and wherein the filter membrane in step (3) is a polycarbonate filter membrane.

13. The method according to claim 6, wherein in step (2), the ratio of phospholipid, cholesterol and phospholipid-PEG added is 3:1:1 by weight, and the moles of phospholipid-PEG-c(RGD-ACP-K) added account for 8% of the moles of phospholipid-PEG added.

14. The method according to claim 11, wherein the dialysis in step (1) is carried out with a dialysis bag having a molecular weight cutoff of 1000 Daltons.

15. A long-circulating liposome obtained by the method according to claim 6.

16. A method for treating cancer, comprising administering a therapeutically effective amount of the long-circulating liposome according to claim 1, wherein said cancer is selected from the group consisting of acute leukemia; malignant lymphoma; breast cancer; lung cancer; prostate cancer; and melanoma.

17. The long-circulating liposome according to claim 1, wherein said chemical bond is covalent bond.

18. The method according to claim 6, wherein said anti-cancer agent is doxorubicin hydrochloride.

19. The method according to claim 11, wherein in step (2), the ratio of phospholipid, cholesterol and DSPE-PEG2000 added is 3:1:1 by weight, and the moles of DSPE-PEG2000-c(RGD-ACP-K) added account for 8% of the moles of DSPE-PEG2000 added.

* * * * *